United States Patent [19]
van Leer

[11] 3,991,757
[45] Nov. 16, 1976

[54] HYPODERMIC SYRINGE
[75] Inventor: Oscar Jacques van Leer, Amstelveen, Netherlands
[73] Assignee: Koninklijke Emballage Industrie van Leer, BV, Amstetveen, Netherlands
[22] Filed: June 16, 1975
[21] Appl. No.: 587,051

[30] Foreign Application Priority Data
June 17, 1974 Netherlands.................... 7408071

[52] U.S. Cl................................ 128/216; 222/92
[51] Int. Cl.² ......................................... A61M 5/00
[58] Field of Search .......... 128/216, 215, 218, 224, 128/231, 232, 233; 222/92–95, 106, 107; 401/160, 9, 152, 153

[56] References Cited
UNITED STATES PATENTS
2,667,165  1/1954  Smith................................. 128/216
2,717,598  9/1955  Krasno............................... 128/216
2,771,879  11/1956  Salisbury, Jr. ...................... 128/216
3,473,524  10/1969  Drewe............................. 128/216 X Primary Examiner—John D. Yasko
Attorney, Agent, or Firm—Stevens, Davis, Miller & Mosher

[57] ABSTRACT

Hypodermic syringe consisting of a compressible reservoir of a material at least partly consisting of a thermoplastic synthetic material, which reservoir is coupled to a hypodermic needle and of which one wall is movable towards an opposite wall. The walls are movable with respect to each other and have a common hinge-point in the manner of a pointed bellows. The walls are coupled with each other and with a third collapsible wall via folding straight lines acting as hinges. The material of the reservoir is treated such at least on the spot of these folding lines, that it tries to move the mutually movable walls toward each other.

7 Claims, 17 Drawing Figures

FIG.-15
FIG.-14
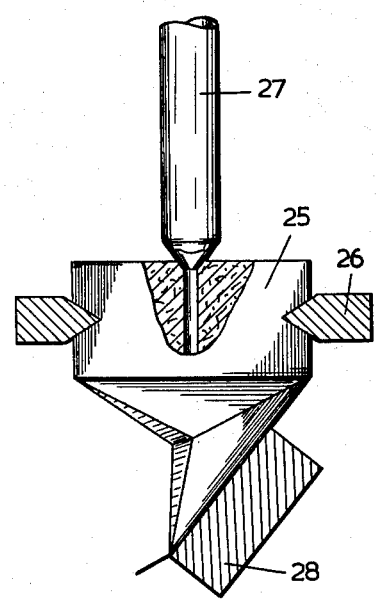
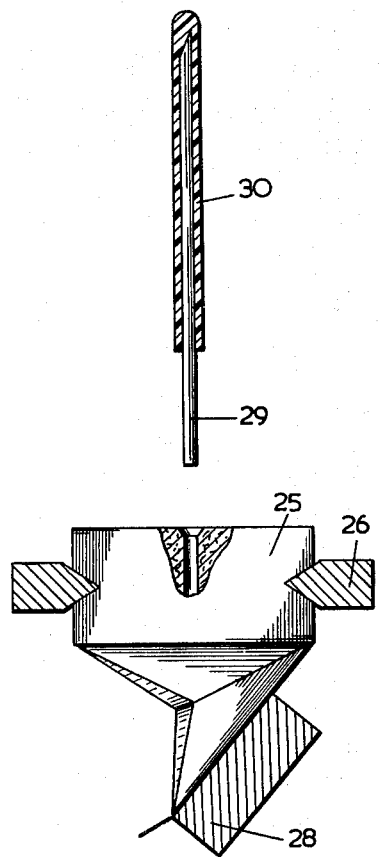

HYPODERMIC SYRINGE

The invention relates to a hypodermic syringe consisting of a compressible reservoir of a material at least partly consisting of a thermoplastic synthetic material, which reservoir is coupled to a hypodermic needle and of which one wall is movable towards an opposite wall. Such a hypodermic syringe is known for instance from the published Dutch Patent Application No. 283,370.

Purpose of the invention is to provide a hypodermic syringe which can be manufactured in a most simple manner, which is easy to handle and which with certainty always is completely filled with liquid and remains filled with liquid.

According to the invention this purpose is achieved in that these walls, movable with respect to each other, have a common hinge-point in the manner of a pointed bellows, which walls are coupled with each other and with a third collapsible wall via folding lines acting as hinges, the material of the reservoir being treated such, at least on the spot of these folding lines, that it tries to move the mutually movable walls towards each other. With the embodiment described, showing a resemblance with a bellows in that two tapering walls can be moved towards each other by folding the connecting wall or walls, it is achieved that the entire contents can be removed from the reservoir with substantially constant outflow and constant pressure. Because the folding lines, acting as hinges, are treated such that they try to move the walls towards each other, a constant slight pressure is exerted upon the contents, the result of which being that the infiltration of air is opposed. This is achieved in a simple manner by compressing the empty reservoir and doing this in hot condition and to fix this condition by cooling. The filled reservoir then always tends to return into this fixed condition in which the reservoir is empty. Other methods for fixing a memory in the thermoplastic resin can be applied as well.

According to the invention the reservoir preferably has the shape of a spatial polygon, determined by similar triangles, four of which are identical and meeting on one point the sides which determine the base-angle of each triangle, which point forms the hinge-point and of which the non-coinciding sides coincide with the hypotenuses of the four mutually identical right-angled triangles forming the collapsible wall and of which the right-angled sides, meeting in one point, form the folding lines and which by twos form the same surface as each of the four triangles mentioned before. The two walls movable towards each other and meeting in the point then each consist of two triangles forming a small angle with each other and consequently having a fair degree of solidity, whereas the third wall is easily collapsible by the intersecting folding lines. In this way a form is obtained which can easily be emptied between the fingers of one hand. It is also possible to divide an other wall, determined by two triangles with coinciding base, into four right-angled triangular surfaces by a folding line lying transversely on said base. The collapse then can take place in two manners.

Preferably all triangular surfaces are isosceles right-angled triangles, the four of which, forming the collapsible wall, have the same united surface like that of each of the walls movable towards each other.

The needle is preferably placed or suitable for placing near the sharp point of the spatial polygon, which polygon is opposite the collapsible wall.

However, it is also possible to place the needle in the holder which is at the side of one of the mutually movable walls. The holder for the needle preferably consists of a flat strip directed to the common hinge-point of the walls movable towards each other. In this way the hypodermic syringe can easily be held between two fingers supporting the lower wall and with a third finger pressure can be exerted upon the upper wall to empty the syringe. Moreover, a gripping surface is obtained with which the hypodermic needle can be firmly held during the injection without exerting pressure upon the reservoir.

The invention also relates to a method for the manufacture of the hypodermic syringe. Herewith it is started from a flat tube which is closed by welding transversely upon the longitudinal axis, and is, respectively is being, provided with folding lines intersecting according to the diagonals of a rectangle at both sides above this weld, whereby welding strips are left clear above the intersection of the folding lines, after which the welding strips are pressed together and welded and thereafter the top is pressed flatly against the transverse weld by applying heat and by folding the third wall and is cooled in this position. The reservoir then has obtained the property of constantly trying to take up the entirely empty position which opposes infiltrations of air.

It is possible as well to manufacture the blank for the reservoir and needle holder as one piece by injection molding.

The invention now will be elucidated on the basis of the drawings.

Figure 4A:
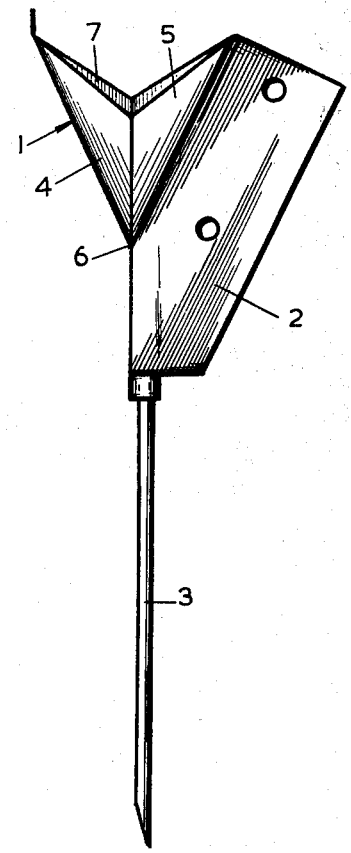
Figure 4B:
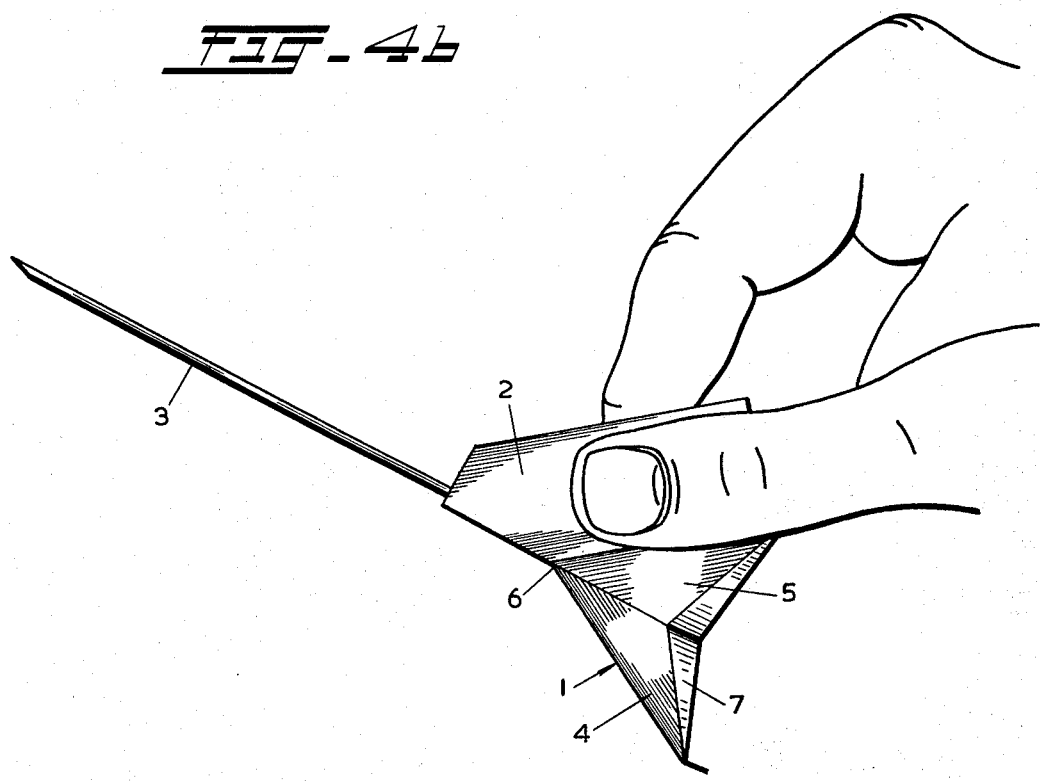
Figure 4C:
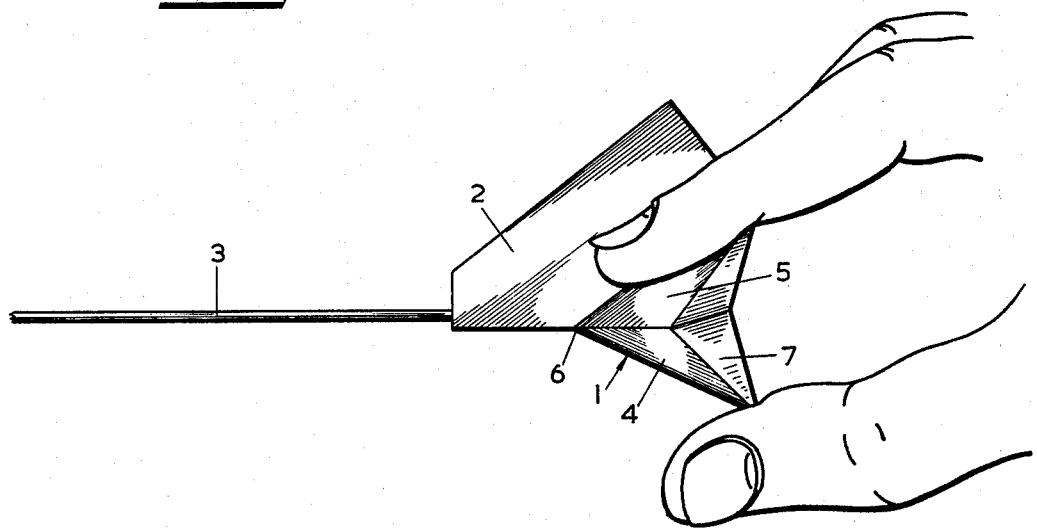
Figure 5:
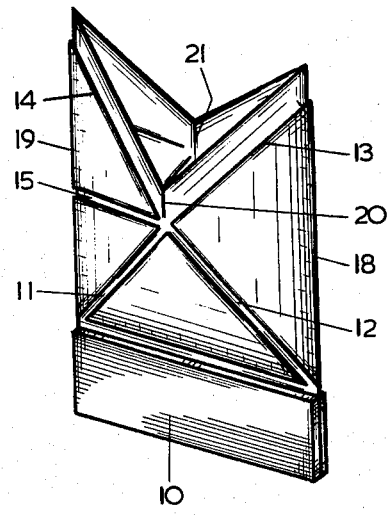
Figure 6:
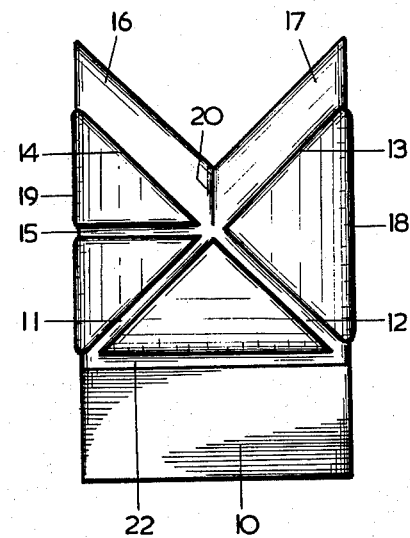
Figure 7:
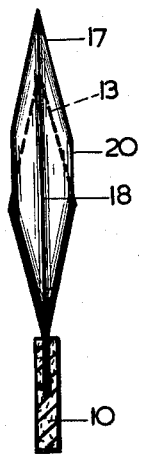
Figure 8:
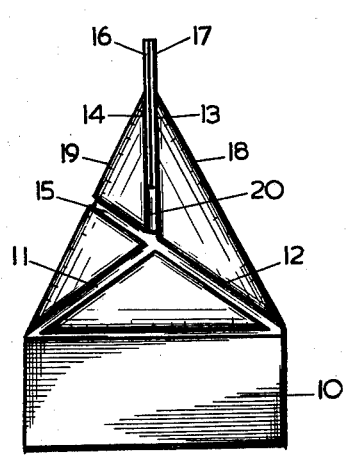
Figure 9:
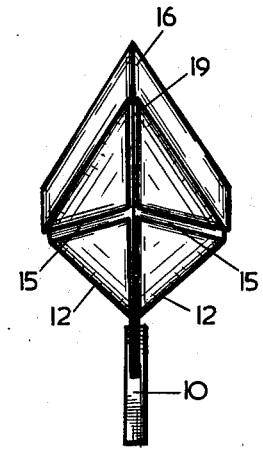
Figure 10:
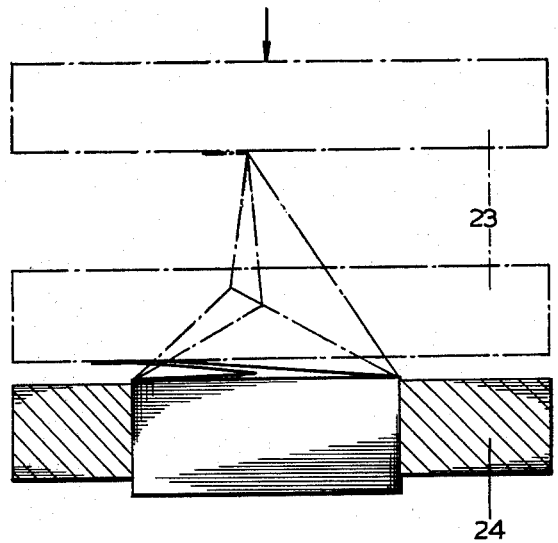
Figure 11:
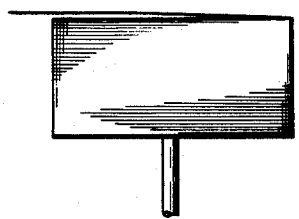
Figure 12:
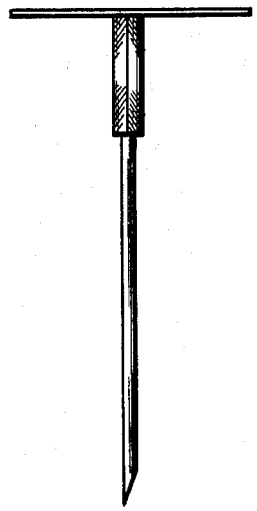
Figure 13:
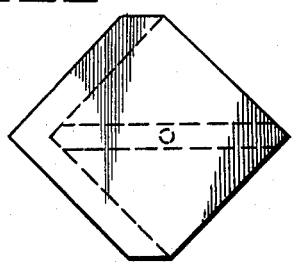

FIGS. 4a to 4c inclusive show an other embodiment of the hypodermic syringe and its manner of operation;

FIG. 5 shows in perspective the initial work-piece for the manufacture of the reservoir of the hypodermic syringe;

FIGS. 6 and 7 show the same initial work-piece in front and side-view;

FIGS. 8 and 9 show the closed work-piece or reservoir in front and side-view;

FIG. 10 shows a phase from the manufacture of the reservoir;

FIGS. 11, 12 and 13 are various views of the hypodermic syringe with completely compressed and emptied reservoir;

FIG. 14 shows the filling of the reservoir and

FIG. 15 shows the connection of a needle with a filled reservoir.

Figure 1:
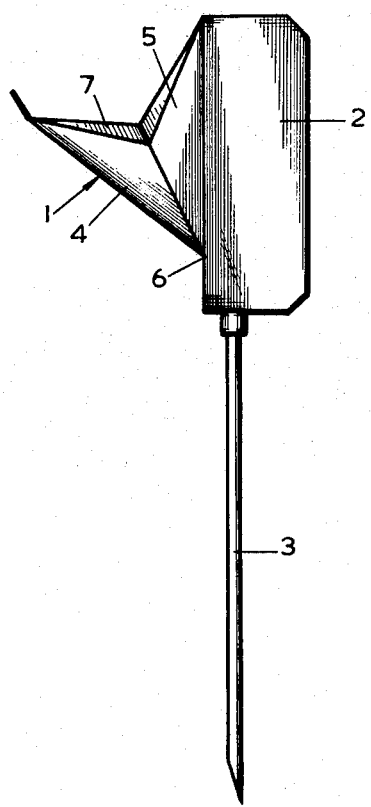
FIG. 1 shows an embodiment of the hypodermic syringe according to the invention.

The hypodermic needle, shown in FIG. 1, consists of a reservoir 1, the holder 2 and the needle 3. The reservoir 1 consists of the mutually movable walls 4 and 5 which are composed of triangles and which meet in the point 6 where the connection with the needle 3 is and which are connected with each other by the collapsible wall 7 at the side turned away from the point.

Figure 2:
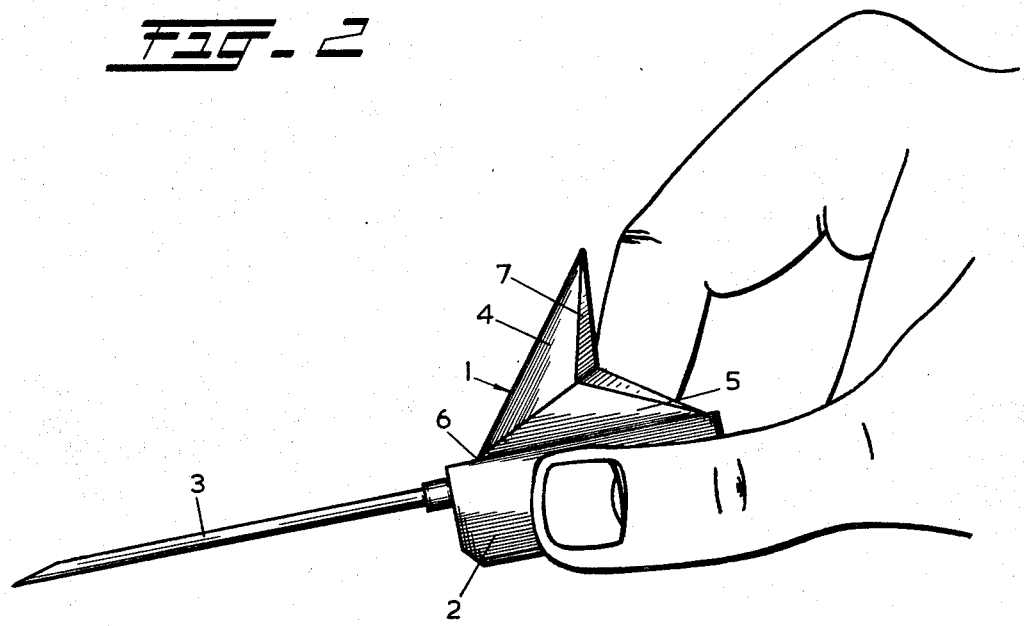
FIGS. 2 and 3 show how the hypodermic syringe of FIG. 1 should be handled.

FIG. 2 shows the way in which the hypodermic needle should be gripped at the holder 2 to insert the needle.

Figure 3:
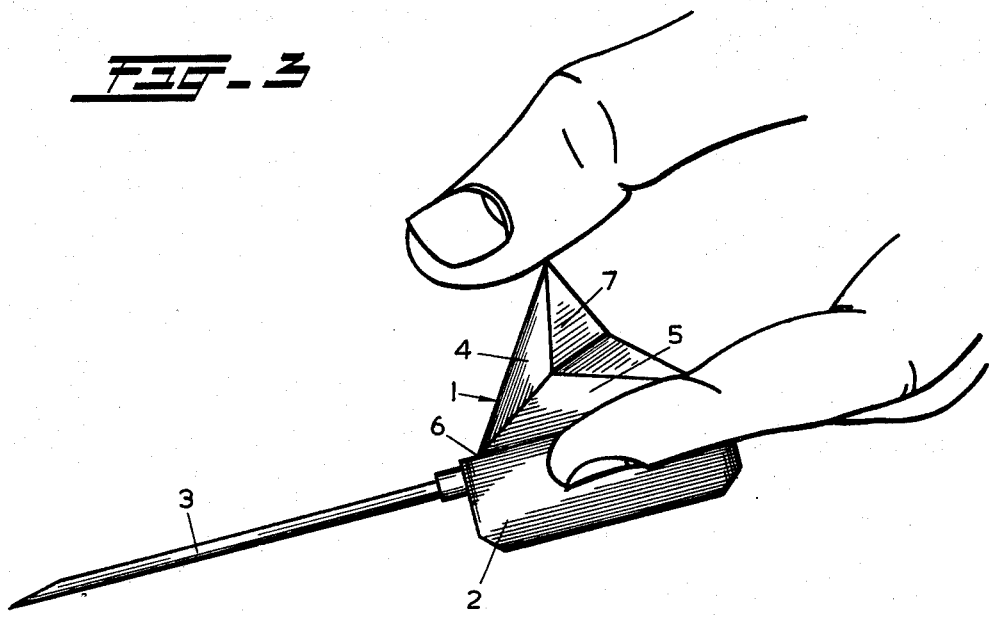

FIG. 3 shows how to place the fingers after insertion of the needle to empty the reservoir.

The reservoir 1 resembles a bellows.

The embodiment, shown in FIGS. 4a to 4c inclusive, differs from the embodiments of the preceding Figures by the disposal of the needle, which now extends at an angle with the folding line adjacent to the reservoir.

FIG. 5 shows in perspective an initial work-piece, which can be used in the manufacture of the hypodermic syringe according to the invention. FIG. 5 shows a flat tube closed by welding at 10 eventually including an element, not shown, for connecting it to the needle.

Above this weld 10 the tubular material is provided with folding lines 11 to 14 inclusive at both sides as well as with an extra folding line 15.

FIG. 6 shows the front-view of this work-piece and FIG. 7 shows the corresponding side-view from which the still almost flat form is clearly apparent.

FIG. 8 shows the position of the surfaces folded according to the folding lines 11 to 14 inclusive in which the edged 16 and 17 are flatly superposed and welded together.

From the corresponding side-view, shown in FIG. 9, it appears that the holder has become wider.

Apart from the folding lines already mentioned other folding lines are shown at 18, 19, 20, 21 and 22 which are necessary to bring about the form shown in FIGS. 8 and 9 (vide FIG. 5).

From the Figures it appears that the reservoir is composed of triangular planes, all being equal to each other, and the triangular planes with the folding line 15 are divided in two by the said line.

FIG. 10 shows a following phase in the manufacture of the reservoir. It is started from the condition as shown in FIGS. 8 and 9.

The reservoir, shown in FIG. 10, is now clamped in the manner as shown there between hot plates 23 and 24, which are moved towards each other, so that the reservoir is brought from the condition indicated with interrupted lines into the condition indicated with a drawn line. In this condition the thermoplastic material is cooled so that the reservoir has the form as indicated in FIGS. 11 to 13 inclusive in front-view, side-view and top-view.

Such a reservoir can now be filled in the manner as shown in FIG. 14 provided that there is a channel in the flat portion, forming the holder, which channel supplies a connection with the interior.

For that purpose the holder 25 is clamped into a clamp 26 and the reservoir is filled under pressure from a supply conduit 27, an abutment 28 taking care that the reservoir is not folded open too much.

FIG. 15 shows how with such a filled reservoir the needle can be adjusted. This needle 29 is provided with a protecting casing 30. Other provisions to interconnect needle and reservoir are possible as well.

Apart from the folding line 15 shown in the FIGS. 6 and 8, it is also possible to make a similar folding line as the folding line 15 in the opposite plane limited by the folding lines 12, 13 and 18, so that the top of the reservoir can be turned to the one side as well as to the other side.

Although all triangles, determining the side walls of the spatial polygon, are identical isosceles right-angled triangles, which at least at the place of one wall by the folding line 15 are divided in mutual identical smaller triangles, it is imaginable to use non-isosceles triangles in the side-planes which triangles diverge from the form of the triangles in the lower plane. It also is imaginable to make the side-planes from isosceles non-right-angled triangles.

What we claim is:

1. Hypodermic syringe consisting of a compressible reservoir of a material at least partly consisting of a thermoplastic synthetic material, which reservoir is coupled to a hypodermic needle and of which one wall is movable towards an opposite wall, said walls, movable with respect to each other, having a common hinge-point in the manner of a pointed bellows, which walls are coupled with each other and with a third collapsible wall via folding lines acting as hinges, the material of the reservoir being treated such at least on the spot of these folding lines, that it tries to move the mutually movable walls towards each other.

2. Hypodermic syringe according to claim 1, wherein the reservoir has the shape of a spatial polygon, determined by similar triangles, four of which are identical and meeting on one point the sides which determine the base-angle of each triangle, which point forms the hinge-point and of which the non-coinciding sides coincide with the hypotenuses of the four mutually identical right-angled triangles forming the collapsible wall and of which the right-angled sides, meeting in one point, form the folding lines and which by twos form the same surface as each of the four triangles mentioned before.

3. Hypodermic syringe, according to claim 2, wherein at least one other wall, determined by two triangles with coinciding base, is divided into four right-angled triangular planes by a folding line transversely upon that base.

4. Hypodermic syringe according to claim 3, wherein all triangular planes are isosceles right-angled triangles.

5. Hypodermic syringe according to claim 2, wherein the needle is placed near that sharp point of the spatial polygon, which lies opposite the collapsible wall.

6. Hypodermic syringe according to claim 1, wherein the needle is placed in a holder which lies at the side of one of the mutually movable walls.

7. Hypodermic syringe according to claim 6, wherein the holder of the needle consists of a flat strip directed to the common hinge-point of the mutually movable walls.

* * * * *